(12) United States Patent
Grassi et al.

(10) Patent No.: US 7,723,542 B2
(45) Date of Patent: May 25, 2010

(54) PROCESS FOR THE PREPARATION OF ALKYL- AND ARYL-DIPHOSPHONIC ACIDS AND SALTS THEREOF

(75) Inventors: Simona Grassi, Saronno (IT); Anna Volante, Milan (IT)

(73) Assignee: Trifarma S.p.A. (IT)

( * ) Notice: Subject to any disclaimer, the term of this patent is extended or adjusted under 35 U.S.C. 154(b) by 877 days.

(21) Appl. No.: 10/584,022

(22) PCT Filed: Dec. 22, 2004

(86) PCT No.: PCT/EP2004/014556

§ 371 (c)(1),
(2), (4) Date: Oct. 25, 2006

(87) PCT Pub. No.: WO2005/063779

PCT Pub. Date: Jul. 14, 2005

(65) Prior Publication Data

US 2007/0112197 A1    May 17, 2007

(30) Foreign Application Priority Data

Dec. 23, 2003  (IT) .......................... MI2003A2582
Jan. 22, 2004  (IT) .......................... MI2004A0080

(51) Int. Cl.
*C07F 9/38*      (2006.01)
(52) U.S. Cl. ............................ 564/15; 546/22; 548/119
(58) Field of Classification Search ................. 564/15; 546/22; 548/119
See application file for complete search history.

(56) References Cited

U.S. PATENT DOCUMENTS

| | | | | |
|---|---|---|---|---|
| 4,407,761 A | * | 10/1983 | Blum et al. ................... | 562/13 |
| 4,927,814 A | * | 5/1990 | Gall et al. .................... | 514/108 |
| 4,939,130 A | | 7/1990 | Jaeggi et al. .................. | 514/94 |
| 5,583,122 A | | 12/1996 | Benedict et al. ............... | 514/89 |
| 7,038,083 B2 | * | 5/2006 | Lidor-Hadas et al. ......... | 564/15 |

FOREIGN PATENT DOCUMENTS

| | | |
|---|---|---|
| DE | 26 58 961 | 6/1978 |
| DE | 27 02 631 | 7/1978 |
| DE | 3 623 397 | 1/1988 |
| EP | 0 252 504 | 1/1988 |
| EP | 1 243 592 | 6/2005 |
| IT | 1 230 503 | 10/1991 |

OTHER PUBLICATIONS

Hancock et al., 'Characteristics and Significance of the Amorphous State in Pharmaceutical Systems', Journal of Pharmaceutical Sciences, Jan. 1997, vol. 86, No. 1, pp. 1-12.*
Widler L. et al: "Highly potent geminal biphosphonates. From Pamidronate Disodium (Aredia) to Zoledronic acid (Zometa)" Journal of Medicinal Chemistry, American Chemical Society. Washington U.S. vol. 45, No. 17 Aug. 15, 2002, pp. 3721-3738, XP001164243 ISSN: 0022-2623.
Kieczykowski et al: "Preparation of (4-Amino-1-Hydrobutylidene) bisphosphonic Acid Sodium Sal, MK-217 (Alendronate Sodium). An improved Procedure for the Preparation of 1-Hydroxy-1, -bisphosphonic Acids" journal of Organic Chemistry, Samerican Chemical Society. Easton, US vol. 60, 1995, pp. 8310-8312, XP002310243 ISSN: 0022-3263.
International Search Report PCT/EP2004/014556 dated May 11, 2005.

* cited by examiner

*Primary Examiner*—Peter G O'Sullivan
(74) *Attorney, Agent, or Firm*—Ostrolenk Faber LLP

(57) ABSTRACT

The invention relates to a process for the preparation of diphosphonic acids by reaction of a carboxylic acid with a mixture of phosphorous acid and phosphorus oxychloride in defined molar ratios and in the absence of solvents. The invention further relates to ibandronic acid monosodium salt in the amorphous form.

13 Claims, No Drawings

PROCESS FOR THE PREPARATION OF ALKYL- AND ARYL-DIPHOSPHONIC ACIDS AND SALTS THEREOF

CROSS REFERENCE TO RELATED APPLICATIONS

The present application is a 35 U.S.C. § 371 national phase conversion of PCT/EP2004/014556 filed Dec. 22, 2004, which claims priority of Italian Application No. MI2003A002582, filed Dec. 23, 2003 and Italian Application No. MI2004A000080, filed Jan. 22, 2004.

FIELD OF THE INVENTION

The present invention relates to a process for the preparation of diphosphonic acids, in particular risendronic, zoledronic and ibandronic acids. The invention further relates to ibandronic acid monosodium salt in the amorphous form, pharmaceutical compositions and a process for the preparation thereof.

BACKGROUND OF THE INVENTION

Diphosphonic acids or salts thereof are used in therapy to inhibit bone reabsorption.

Monosodium ibandronate, for example, is used in particular for the treatment and prevention of osteoporosis, neoplasms-associated hypercalcemia, Paget's disease and related pathologies.

Monosodium ibandronate is currently available on the market in the anhydrous [RN=138844-81-2] and monohydrate [RN=138926-19-9] crystalline form.

The preparation of ibandronic acid and salts thereof is disclosed in U.S. Pat. No. 4,927,814 and DE 3623397.

One of the main problems related to the synthesis of diphosphonic acids is the solidification of the reaction mixture, which makes it difficult to carry out the reaction on an industrial scale and does not provide satisfactory yields (yields are generally of about 50%).

In particular, the production of risedronic, zoledronic and ibandronic acid requires starting materials that are costly and not easily available.

U.S. Pat. No. 4,927,814 discloses the preparation of 1-hydroxy-3-(N-methyl-N-pentylamino)propane-1,1-diphosphonic acid (ibandronic acid) by reaction of 3-(N-methyl-N-pentylamino)propionic acid with phosphorus trichloride and phosphorous acid in chlorobenzene. At the end of the reaction the solvent is removed by decantation and the resulting solid mass is first hydrolyzed with hydrochloric acid, then filtered, concentrated to a semifluid mass and purified through a resin (Amberlite IR 120). These operations are particularly difficult and dangerous when carried out on an industrial scale.

U.S. Pat. No. 5,583,122 discloses 1-hydroxy-2-(3-pyridyl) ethane-1,1-diphosphonic acid (risedronic acid), but its preparation is not exemplified. On the contrary, the patent discloses the synthesis of an isomer, 1-hydroxy-2-(2-pyridyl)ethane-1,1-diphosphonic acid, by reaction of (2-pyridyl)acetic acid with phosphorous acid and phosphorus trichloride in chlorobenzene. At the end of the reaction the mixture solidifies and the solvent must be removed by decantation. This operation is difficult to carry out on an industrial scale and the addition of water necessary to hydrolyse the solid mass is dangerous. Yield amounts to 52%.

EP 1243592 discloses the synthesis of risedronic acid following the same general procedure as U.S. Pat. No. 5,583, 122, starting from (3-pyridyl)acetic acid hydrochloride. The product is isolated in a 50% yield, without adding solvents to promote precipitation.

U.S. Pat. No. 4,939,130 discloses the synthesis of 1-hydroxy-2-(1-imidazolyl)ethane-1,1-diphosphonic acid (zoledronic acid) by reaction of (1-imidazolyl)acetic acid hydrochloride with phosphorus trichloride and 85% phosphoric acid in chlorobenzene. Also in this case a semisolid mass separates from the reaction mixture and chlorobenzene must be decanted off.

J. Org. Chem. 1995, 60, 8310-8312, states that the use of phosphorus oxychloride and phosphorous acid causes solidification of the reaction mixture.

IT 1230503 discloses the preparation of 8-amino-1-hydroxyoctane-1,1-diphosphonic acid by reaction of 8-aminooctanoic acid with a mixture of phosphorous acid and phosphorus trichloride, with or without solvents. When no solvent is used, the optimal 8-amino-octanoic acid: phosphorous acid: phosphorus trichloride molar ratio is 1:3:1.5.

SUMMARY OF THE INVENTION

It has now been found that the reaction of a carboxylic acid with phosphorus oxychloride and phosphorous acid in well-defined ratios always leads to a fluid mass that can be thoroughly stirred and is suitable for industrial production.

Accordingly, the present invention relates to a process for the preparation of diphosphonic acids of the general formula (I)

$$R-(CH_2)_m-\underset{\underset{O}{\overset{\parallel}{P}}\diagdown_{OH}^{OH}}{\overset{HO\diagdown\underset{\parallel}{\overset{O}{P}}-OH}{|}}$$

(I)

wherein
m is an integer from 1 to 8 and
R is a residue of formula $$R_1\diagdown_{R_2}^{N-}$$

wherein $R_1$ and $R_2$ are independently selected from hydrogen or $C_1$-$C_5$ alkyl, or R is a 5- or 6-membered aromatic ring, optionally containing one or more heteroatoms selected from N, O, S, preferably imidazolyl or pyridyl, by reaction of a carboxylic acid of the general formula (II)

$$R(CH_2)_mCOOH \quad (II)$$

wherein R and m are as defined above, with a mixture of phosphorous acid and phosphorus oxychloride, in the absence of solvents and with a carboxylic acid:phosphorus oxychloride: phosphorous acid molar ratio of 1:2-4:8-12, preferably of 1:3:10. The process is particularly suitable for the preparation of the following acids:

ibandronic acid (m=2, R =$R_1R_2$N- wherein $R_1$=$CH_3$ $R_2$=$CH_3(CH_2)_4$)

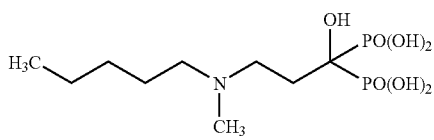

zoledronic acid (m=1, R=imidazol-1-yl)

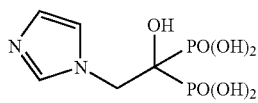

risedronic acid (m=1, R =pyrid-3-yl)

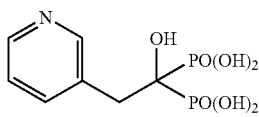

and is particularly advantageous in that, thanks to the absence of solvents and to the fluidity of the reaction mixture, not only does it not involve high risk, but it also gives much higher yields than those reported in the literature, usually of 60% or more.

Ibandronic acid obtained with the method of the invention can be conveniently transformed into the sodium salt, in particular the amorphous form, which is a further aspect of the invention. It has in fact been found that the amorphous ibandronic acid monosodium salt is particularly suitable for pharmaceutical use. More particularly, oral pharmaceutical preparations have improved bioavailability compared with those currently available on the market.

Amorphous monosodium ibandronate can be obtained with conventional methods. For example, ibandronic acid can be salified with sodium hydroxide, carbonate or bicarbonate, preferably sodium hydroxide, to give an aqueous solution that, after optional filtration, is lyophilized. As an alternative to lyophilization, the product can be submitted to spray-drying. Monosodium ibandronate thereby obtained is an amorphous white powder with water content lower than 3-4%, usually lower than 2%. Lyophilization and spray-drying conditions (concentration, temperature, time, pressure) are not critical and can be determined according to the production plant.

DETAILED DESCRIPTION OF CERTAIN EMBODIMENTS OF THE INVENTION

Typical operative conditions are shown in the following examples and can be adjusted within wide ranges of the reported values, for instance within a ±20-30% range.

Amorphous monosodium ibandronate thus obtained can be formulated in conventional pharmaceutical preparations, in particular suitable for the oral administration. The doses are the same as those of the formulations already available on the market and can optionally be reduced thanks to the improved bioavailability of the salt.

Examples

The invention will be hereinafter illustrated in more detail by means of some examples.

Example 1

Preparation of Risedronic Acid

A mixture of (3-pyridyl)acetic acid hydrochloride (10 g 0.06 moles) and phosphorous acid (47 g, 0.58 moles) is slowly added with phosphorus oxychloride (28.8 g 0.19 moles). The fluid mixture is warmed up to 60-70° C. for 24 hours, then added with 60 ml water at the same temperature. The mixture is refluxed for 6 hours, added with 0.3 g charcoal and hot-filtered through celite. The clarified solution is added with 160 ml acetone. The resulting precipitate is filtered, suspended in 50 ml water, dissolved at pH 7.5 (+−0.2) with 30% sodium hydroxide. The resulting solution is acidified to pH 0.8 (+/−0.2) and the precipitate is filtered and dried under vacuum at 40-50° C. to constant weight. 9.8 g pure risedronic acid is obtained (yield: 60%).

Example 2

Preparation of Zoledronic Acid

Following the same procedure as in Example 1, using (1-imidazolyl)acetic hydrochloride as the starting material, zoledronic acid is obtained (yield: 62%).

Example 3

Preparation of Ibandronic Acid

Following the same procedure as in Example 1, using 3-(N-methyl-N- pentylamino)propionic acid as the starting material, ibandronic acid is obtained (yield: 59%).

Example 4

Ibandronic acid (10 g) is suspended in water (200 ml) and added with 1M NaOH to pH 4.3-4.4. The resulting clear solution is filtered through a 0.22 micron filter, frozen to −40° C. and lyophilized (<100 mbar, 0-40° C.), to give amorphous monosodium ibandronate with a water content of less than 2%.

Example 5

Ibandronic acid (10 g) is suspended in water (200 ml) and added with 1M NaOH to pH 4.3-4.4. The resulting clear solution is filtered through a 0.22 micron filter and conveyed under pressure to a spray-drier (nozzle temperature=180-200° C.). Amorphous monosodium ibandronate identical to that of Example 1 is obtained.

What is claimed is:

1. A process for the preparation of diphosphonic acids of the general formula (I)

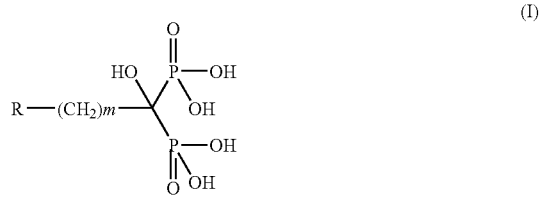

wherein m is an integer from 1 to 8 and

R is a residue of formula

wherein $R_1$ and $R_2$ are independently selected from hydrogen or $C_1$-$C_5$alkyl, or R is a 5- or 6 membered aromatic ring, optionally containing one or more heteroatoms selected from N, O, S, by reaction of a carboxylic acid of the general formula (II)

$$R(CH_2)_m COOH \quad (II)$$

wherein R and m are as defined above, with a mixture of phosphorous acid and phosphorus oxychloride, in the absence of solvents and with a carboxylic acid: phosphorus oxychloride: phosphorous acid molar ratio of 1:2-4:8-12.

2. The process according to claim 1 wherein the carboxylic acid:phosphonis oxychloride: phosphorous acid molar ratio is 1:3:10.

3. The process according to claim 1 for the preparation of diphosphonic acids wherein R is imidazolyl or pyridyl.

4. The process according to claim 1 for the preparation of a diphosphonic acid selected from ibandronic, risedronic and zoledronic acid.

5. Ibandronic acid monosodium salt in the amorphous form.

6. A salt according to claim 1 with a water content lower than 2% by weight.

7. Pharmaceutical compositions containing the salt of claim 5 in admixture with at least one suitable excipient.

8. The process for the preparation of the salt of claim 5 comprising the salification of ibandronic acid with sodium hydroxide, carbonate or bicarbonate in an aqueous solution, followed by lyophilization or "spray-drying" of the resulting aqueous solution.

9. The process according to claim 2 for the preparation of diphosphonic acids wherein R is imidazolyl or pyridyl.

10. The process according to claim 2 for the preparation of a diphosphonic acid selected from ibandronic, risedronic and zoledronic acid.

11. The process according to claim 3 for the preparation of a diphosphonic acid selected from ibandronic, risedronic and zoledronic acid.

12. Pharmaceutical compositions containing the salt of claim 6 in admixture with at least one suitable excipient.

13. The process for the preparation of the salt of claim 6 comprising the salification of ibandronic acid with sodium hydroxide, carbonate or bicarbonate in an aqueous solution, followed by lyophilization or "spray-drying" of the resulting aqueous solution.

* * * * *